United States Patent [19]

Sournac et al.

[11] Patent Number: 5,132,116
[45] Date of Patent: Jul. 21, 1992

[54] TABLETS OF THE HYDROPHILIC MATRIX TYPE BASED ON SALBUTAMOL AND A PROCESS FOR THEIR PREPARATION

[75] Inventors: Michel Sournac; Joël Bougaret, both of Castres, France

[73] Assignee: Pierre Fabre Medicament, Paris, France

[21] Appl. No.: 774,724

[22] Filed: Oct. 18, 1991

Related U.S. Application Data

[63] Continuation of Ser. No. 218,590, Jul. 13, 1988, abandoned.

[30] Foreign Application Priority Data

Jul. 16, 1987 [FR] France .................. 87 10048

[51] Int. Cl.⁵ .............................. A61K 9/26
[52] U.S. Cl. ................... 424/469; 424/464; 424/470; 424/465
[58] Field of Search ............. 424/465, 468, 469, 470, 424/467

[56] References Cited

U.S. PATENT DOCUMENTS

| | | | |
|---|---|---|---|
| 3,987,160 | 10/1976 | Broughton | 424/45 |
| 4,369,172 | 1/1983 | Schor et al. | 424/480 |
| 4,478,819 | 10/1984 | Hercalin et al. | 424/457 |
| 4,784,858 | 11/1988 | Ventouras | 424/469 |
| 4,824,677 | 4/1989 | Shak et al. | 424/467 |
| 4,892,741 | 1/1990 | Ohru et al. | 424/474 |

OTHER PUBLICATIONS

C.A. vol. 107, Nos. 14, 5 Oct. 1987, p. 346 Abstract No. 121004r.

Primary Examiner—Thurman K. Page
Assistant Examiner—Leon R. Horne
Attorney, Agent, or Firm—Blakely, Sokoloff, Taylor & Zafman

[57] ABSTRACT

The present invention relates to tablets of the type which contain a homogeneous dispersion of an active principle based on salbutamol or on one of its derivatives in a hydrophilic matrix, ensuring:

in vitro, long-term release of the active principle, which is constant and independent of pH, over a time interval of about 12 hours, in vivo, uptake kinetics of the active principle by the organism of zero order over a time interval of 6 hours, the said matrix containing at least one swelling agent and a diluent in a weight ratio of swelling agent/diluent lying between 0.2 and 0.6, and being preferably equal to about 0.4.

The present invention also covers the process for the preparation of these tablets.

18 Claims, 5 Drawing Sheets

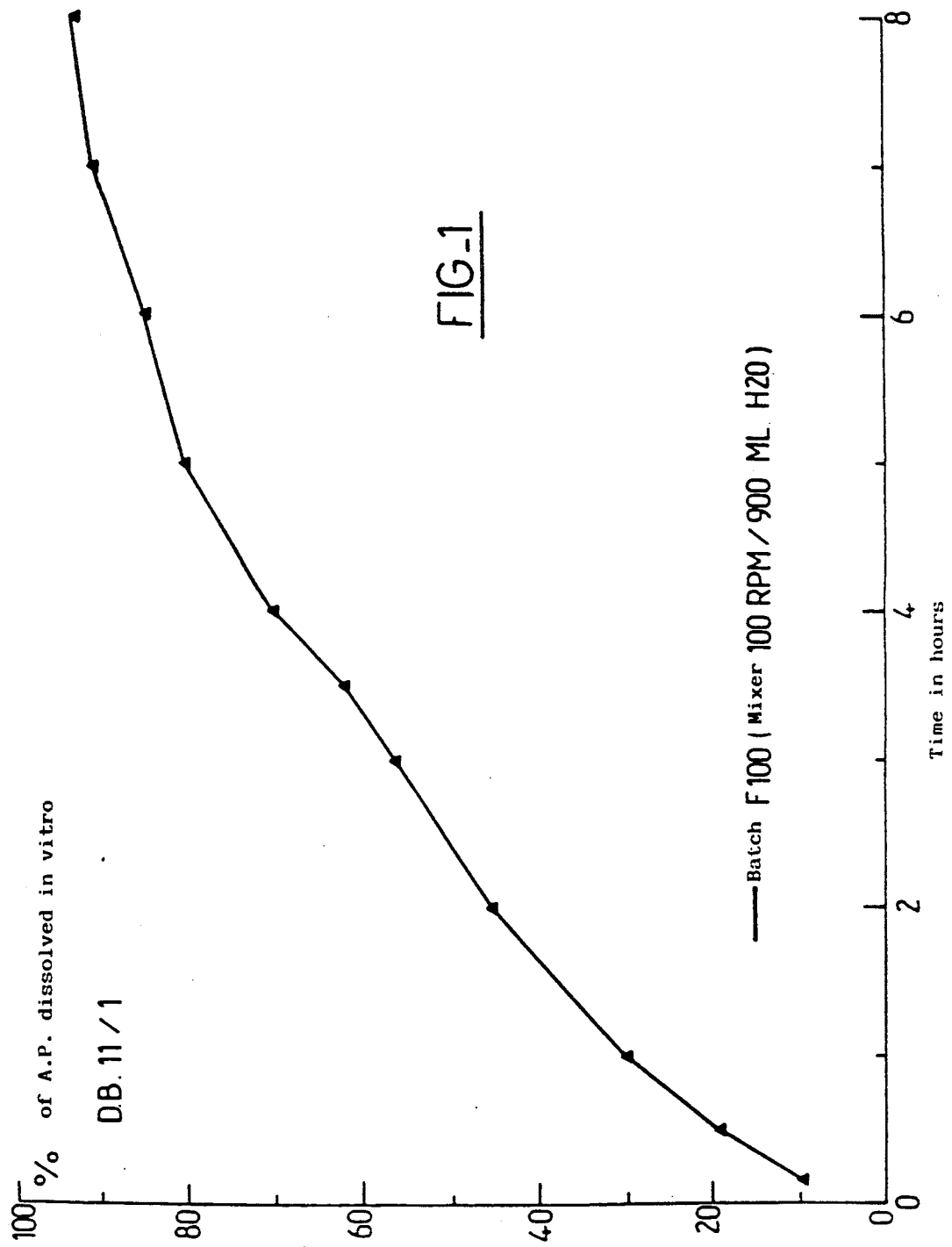

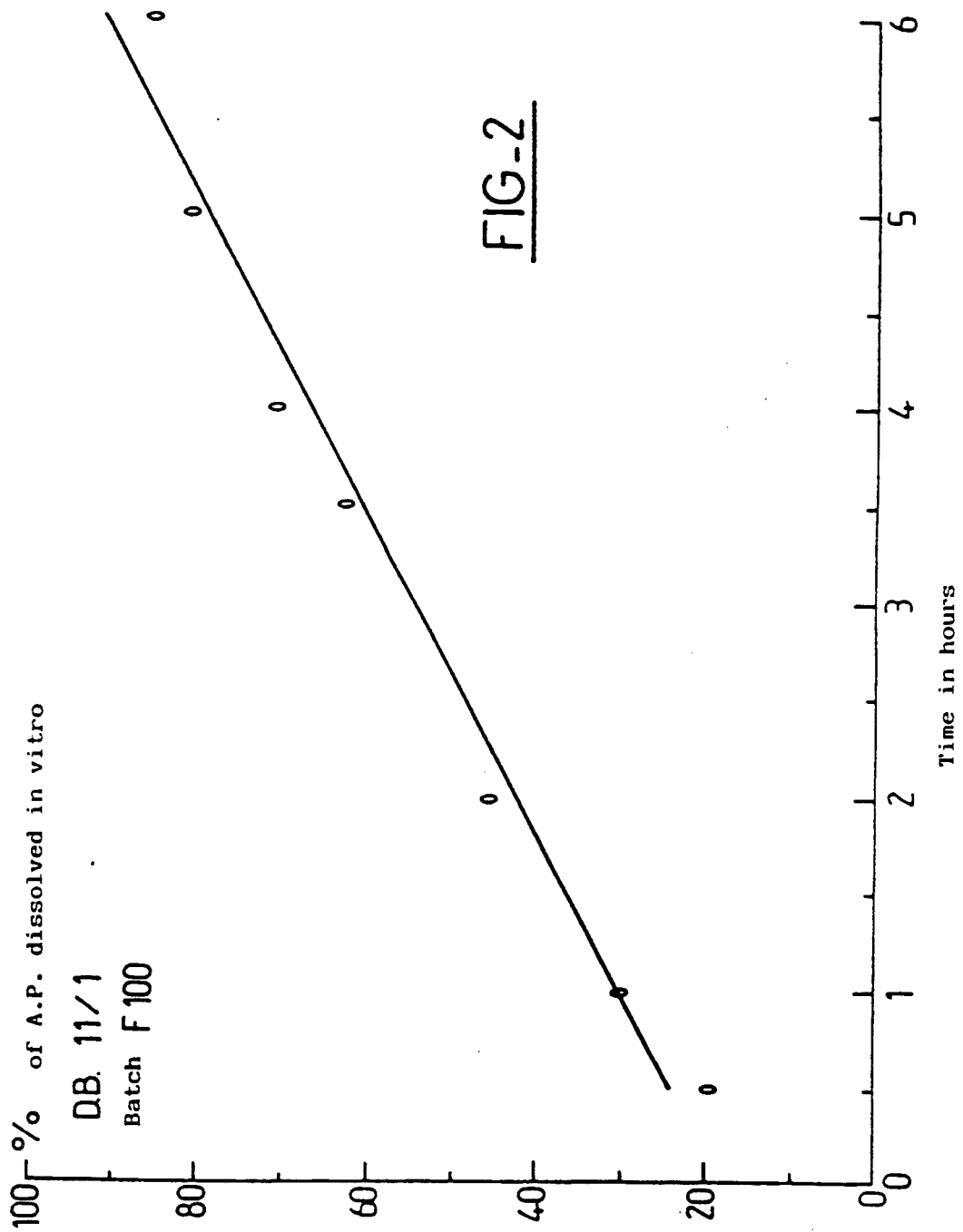

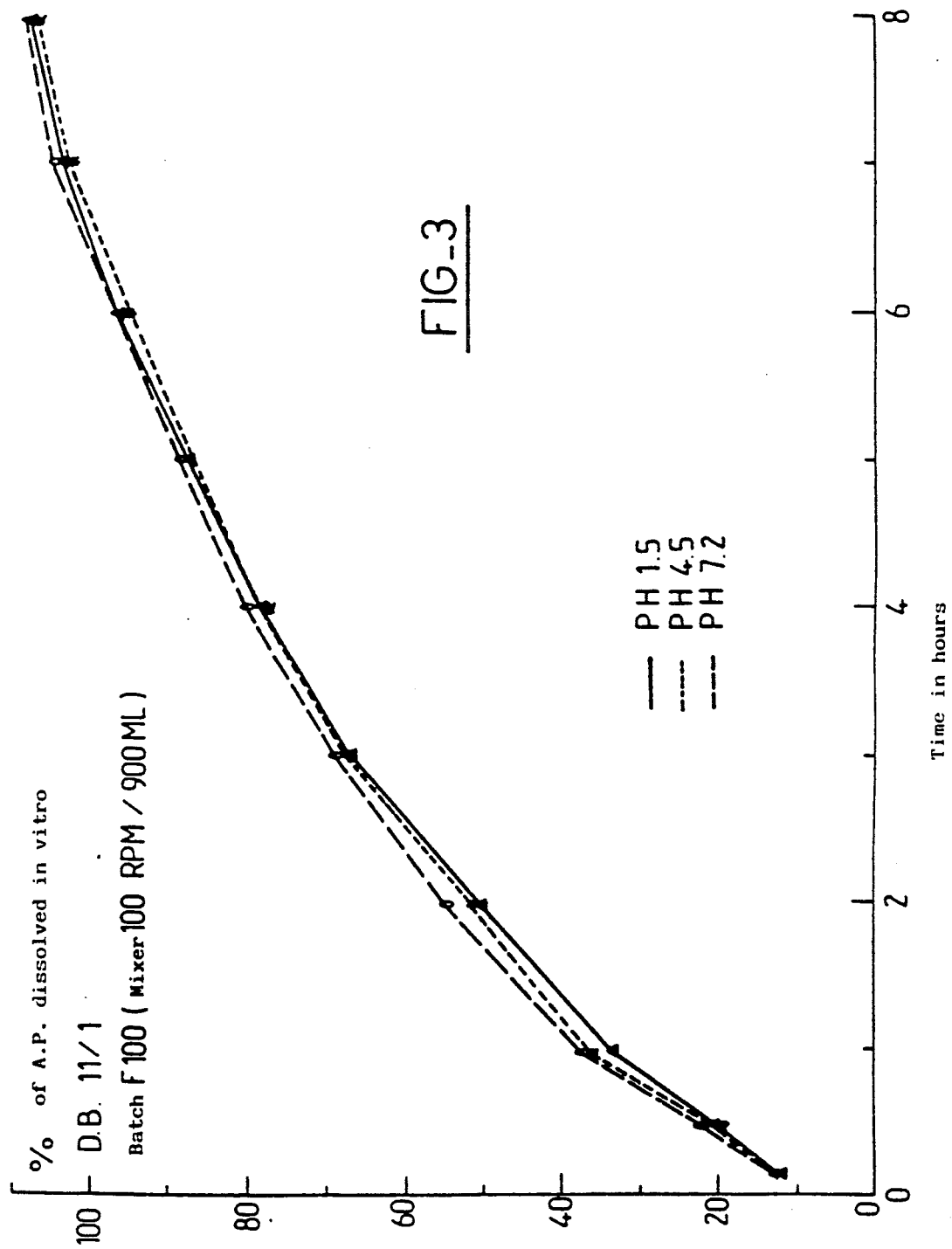

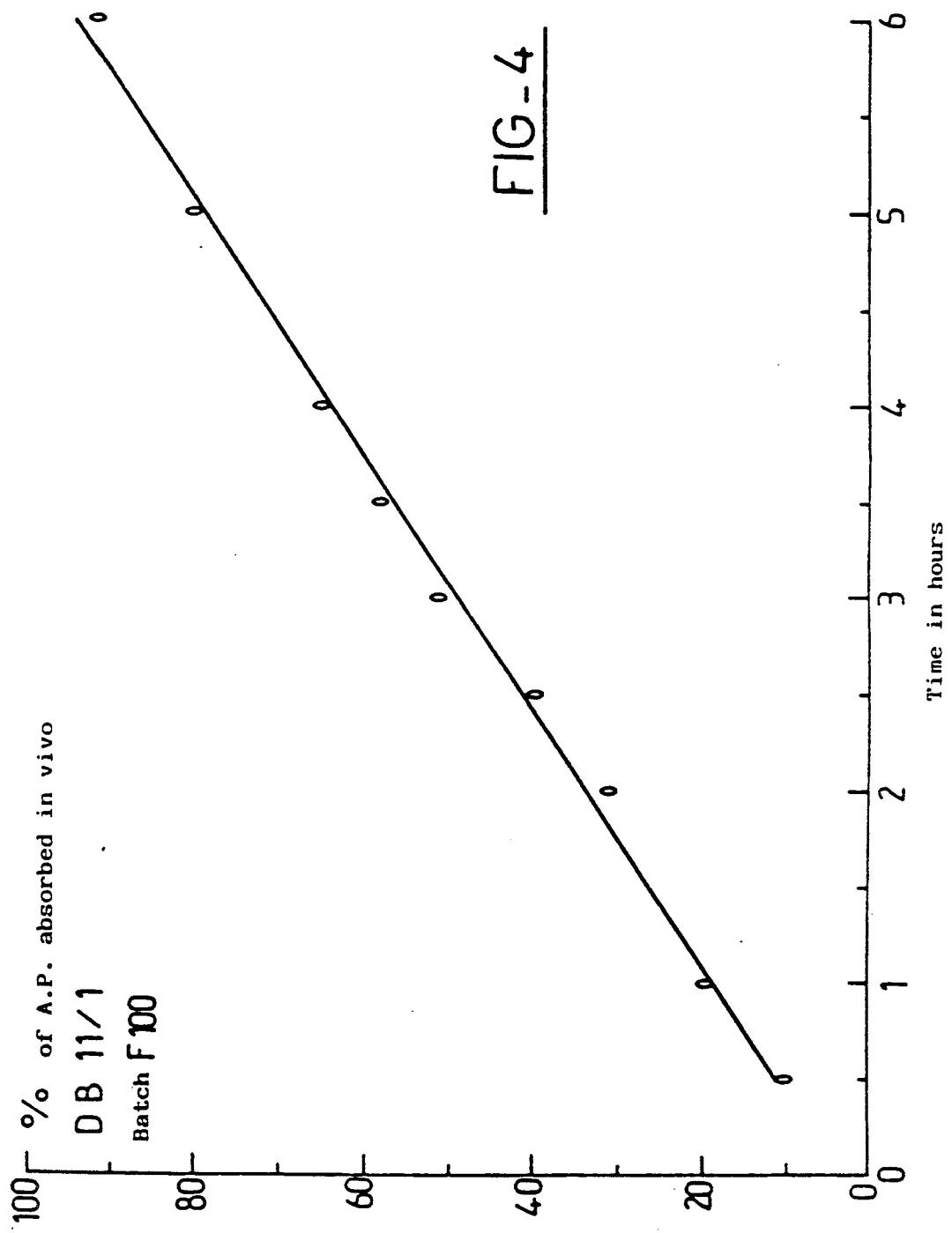

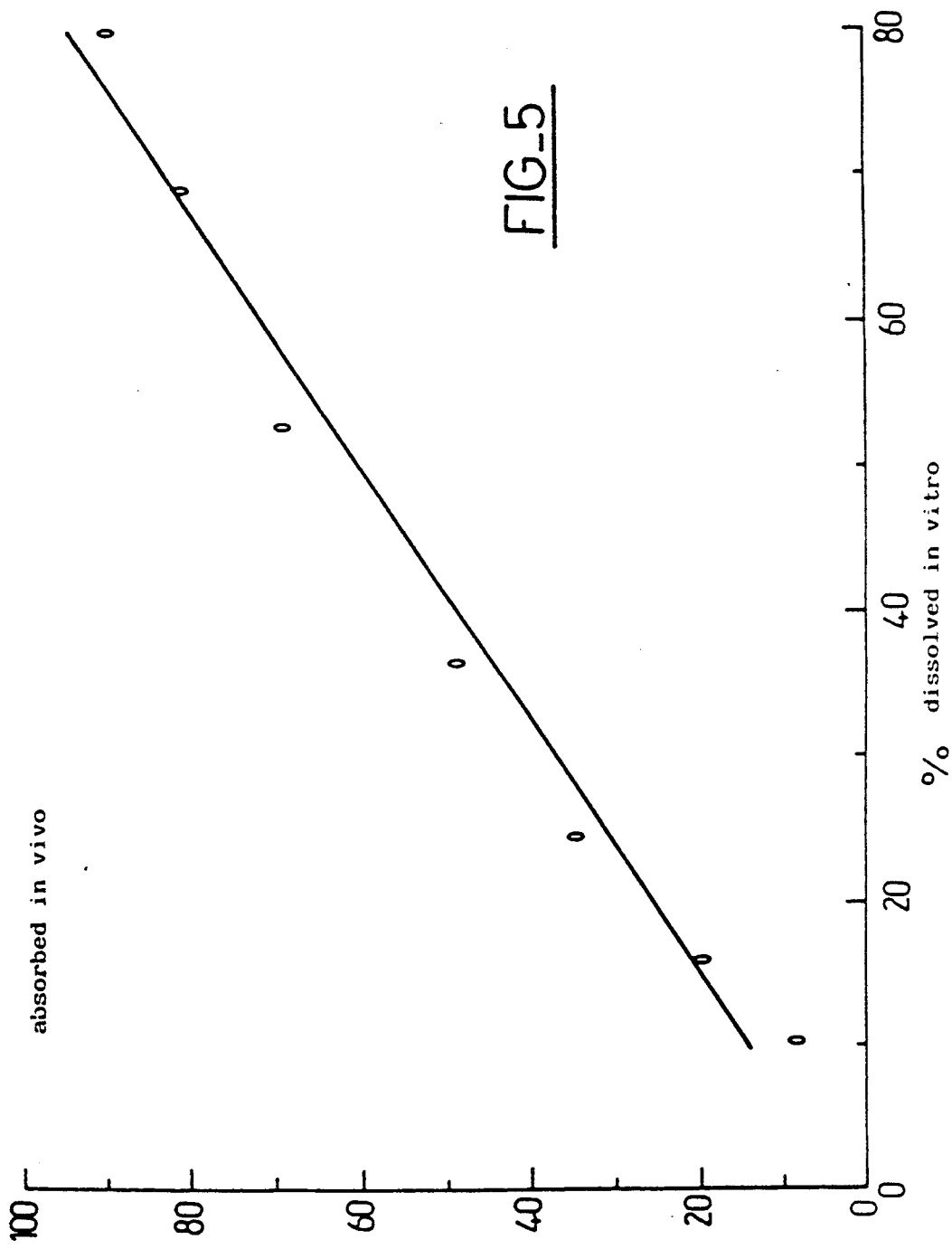
FIG_5

TABLETS OF THE HYDROPHILIC MATRIX TYPE BASED ON SALBUTAMOL AND A PROCESS FOR THEIR PREPARATION

This is a continuation of application Ser. No. 07/218,590 filed Jul. 13, 1988 now abandoned.

The present invention relates to a pharmaceutical composition containing salbutamol or one of its derivatives as active principle and the galenical formulation of which makes the long-term release of this active principle possible.

Salbutamol or [(tert.-butylamino) -2(4-hydroxy-4hydroxymethyl-3-phenyl)-1-ethanol and its derivatives are known to act on the $\beta_2$ receptors of bronchial and uterine smooth muscle (BSM 8010 M). In particular, numerous salbutamol-based specialities exist which are used to treat asthmatic patients.

However, this active principle is easily degraded and much progress has already been made towards the manufacture of stable compositions of salbutamol (FR 83 08722).

Up to now, long-term release forms of such an active principle have not yet been manufactured and marketed on a large scale. Such forms are nonetheless desirable, particularly in the case of the treatment of chronic asthma and the crises it provokes.

That is the reason why the present invention relates to tablets of the hydrophilic matrix type containing a homogeneous dispersion of salbutamol or one of its derivatives and ensuring:

in vitro, long-term release of the active principle, which is constant and independent of pH, over a time interval of about 12 hours, in vivo, uptake kinetics of the active principle by the organism of zero order over a time interval of about 6 hours.

Such a long-term release from containing a suitable dose of active principle (8 mg, for example) is efficacious at a single dose per day. It enables the compliance of the patient to be improved by reducing the number of doses while maintaining therapeutic equivalence with respect to the standard dosage regimen (4 tablets of 2 mg/day).

Furthermore, a single dose in the evening is particularly suited to combatting the nocturnal symptoms of asthma.

This long-term release is achieved by incorporating into the hydrophilic composition at least one swelling agent and a diluent in a weight ratio of swelling agent/diluent lying between 0.2 and 0.6, and preferably being equal to about 0.4.

Preferably, according to the present invention, the diluent (D) contains at least one intrinsic diluent (ID) and one thickening diluent (TD).

Surprisingly, such a combination of TD/ID makes possible the long-term release of the active principle in vitro, in particular from the fourth hour onwards and does so inspite of the high water solubility of salbutamol.

The most efficacious combination from the point of view of this long-term release is found to be that in which the weight ration TD/D is comprised between 0.1 and 0.6.

It is preferable to use as active principle a salt of salbutamol, and in particular the sulfate of salbutamol.

It is particularly advantageous to have recourse to tablets containing from 1 to 10% by weight of active principle (A.P.) with respect to the total weight of the tablet. The preferred weight content of the active principle is equal to about 3% of the total weight of the tablet.

The present invention is characterized, in addition, by the choice of the following constituents: The intrinsic diluent (ID) is preferably chosen from one of more substances which include lactose, sorbitol, mannitol, the phosphates or sulphates of calcium, colloidal silica and/or microcrystalline cellulose. The thickening diluent (TD) is preferably chosen from one or more substances which include starches, starch derivatives, microfine cellulose and/or dextrins.

The swelling agent (S) is preferably chosen from one or more water-soluble polymeric substances giving rise to an apparent viscosity varying between 0.1 and 30 Pa.s at 2% weight/weight at 20° C.

The viscosity is measured with the aid of UBBELHODE tubes. These hydrophilic polymeric substances are preferably chosen from the family of the cellulose and protein hydrocolloids and, in particular, from alginate derivatives, naturally occurring gums, methylcellulose, carboxymethycellulsoe, hydroxypropylcellulose and/or methylhydroxypropylcellulose (MHPC).

The hydrophilic polymer most especially preferred is methylhhdroxypropylcellulose, the viscosity of which is about 15 Pa.s.

Of the naturally occurring gums, it is preferable to use carrageenin.

These polymers can be used alone or in combination.

The tablets according to the present invention contain, in addition, a lubricant such as stearic acid or one of its derivatives, and a pharmaceutically acceptable colouring material: a blue substance is particularly chosen belonging to the family of the synthetic organic lacquers, namely indigotin (code EEC No. 132).

Thus, an example of tablet especially preferred according to the present invention is defined by the following composition:

| | |
|---|---|
| salbutamol sulfate | 9.6 mg |
| methylhydroxypropylcellulose, 15 Pa.s | 86 mg |
| lactose | 150 mg |
| pregelatinized maize starch | 70.9 mg |
| colloidal silica | 2.7 mg |
| magnesium stearate | 2.7 mg |
| indigotin EEC No. 132 | 0.1 mg |
| for a finished tablet of | 322.0 mg |

The tablets according to the present invention are preferably oblong in shape and, possibly, divisible.

The present invention also covers the process which makes possible the manufacture and industrial development of tablets of the type which contain a homogeneous dispersion of salbutamol or one of its derivatives in a hydrophilic matrix containing at least one swelling agent and one diluent.

This process is characterized by the following sequence of steps:

1) sieving of the different components, the swelling agent, the diluent and the active principle;

2) mixing of these components, the swelling agent, diluent and active principle in a weight ratio of swelling agent/diluent lying between 0.2 and 0.6 and a weight of the active principle varying between 1 and 10% by weight of the total weight of the tablet;

3) addition of a lubricant and mixing for about 10 minutes;

4) compression in a rotatory production machine.

The compositions of the different tablets prepared by the process according to the present inventions are given below in Table I as examples in which all of the numerical values refer to mg.

The weight ratios between the different constituents of these tablets are shown in Table. II.

TABLE I

|  | Tablet No. | | | |
| --- | --- | --- | --- | --- |
|  | 1 | 2 | 3 | 4 |
| salbutamol sulfate | 9,6 | 9,6 | 6,0 | 14,40 |
| Lactose | 105,0 | 150,0 | 107,0 | 135,0 |
| dicalcium phosphate |  |  |  | 30,0 |
| pregelatinized maize starch | 64,0 | 70,9 | 36,0 | 105,0 |
| microfine cellulose | 15,0 |  |  | 10,0 |
| MHPC 0,1 Pa.s. |  |  | 8,0 | 40,0 |
| MHPC 4 Pa.s. | 26,0 |  |  |  |
| MHPC 15 Pa.s. | 58,0 | 86,0 | 50,0 | 88,0 |
| Mg stearate | 2,1 | 2,7 | 1,6 | 3,3 |
| colloidal silica | 2,1 | 2,7 | 1,6 | 3,3 |
| lacquer EEC N° 132 | 0,1 | 0,1 | 0,06 | 0,15 |
| unit weight | 281,90 | 322,0 | 210,26 | 429,15 |

TABLE II

|  | Tablet No. | | | |
| --- | --- | --- | --- | --- |
|  | 1 | 2 | 3 | 4 |
| S/D | 0,45 | 0,38 | 0,40 | 0,45 |
| TD/S | 0,94 | 0,82 | 0,62 | 0,89 |
| TD/D | 0,42 | 0,31 | 0,25 | 0,41 |
| A.P./total weight of tablet × $10^{-2}$ | 3,40 | 2,98 | 2,85 | 3,35 |
| A.P./S | 0,114 | 0,110 | 0,103 | 0,112 |
| A.P./D | 0,051 | 0,042 | 0,041 | 0,051 |

As an example, we also give below the results of assays performed in order to determine the kinetics of release of tables No. 2; these results are presented graphically in the following figures:

FIG. 1 presents the kinetics of release in vitro and expresses the progression in the percentage of active principle dissolved as a function of time.

The establishment of standards of release in vitro was carried out with the aid of a homogenizer ( 100 rpm/900 ml of water). The results obtained are as follows:

| % dissolved after 0.17 hour | 3% to 18% |
| --- | --- |
| % dissolved after 1 hour | 20% to 40% |
| % dissolved after 4 hours | 60% to 80% |
| % dissolved after 8 hours | >80% |

FIG. 2 presents a partial interpretation of FIG. 1: a straight line has been drawn through the percentages of active principle dissolved in vitro between 0.5 h and 6 h so as to suggest a constant mean rate of release of the order of 14.21% per hour.

In this figure X represents time (in hours) and Y represents the percentage of active principle dissolved (Regression chosen for the linearization: $Y=AX+B$ with $A=12.16$ and $B=18.09$ Correlation coefficient * $r=0.9884$).

FIG. 3 presents the dissolution in vitro of the active principle as a function of pH.

In this figure: —represents the first curve (medium pH 1.5). Area under the curve=574.11 (trapezoidal method).

.. .. .. .. .. represents the 2nd curve (medium pH 4.5) Area under the curve=573.37 (trapezoidal method).

- - - - - represents the 3rd curve (medium pH 7.2) Area under the curve=588.49 (trapezoidal method).

It can be seen that there is no difference between the kinetics of release at these three different values of pH 1.5. 4.5 and 7.2.

The release of the active principle is thus independent of the pH.

FIG. 4 relates to the kinetics of absorption of salbutamol in vivo (linearization: 0.5 to 6 hours) starting from a tablet of the matrix type. A constant mean rate of absorption is obtained in vivo.

After oral administration of the tables No. 2 to six subjects, the plasma concentrations were interpreted in such a manner as to demonstrate an absorption profile characterized by z zero order uptake up to the sixth hour after ingestion; it follows from this that the constant mean rate of absorption in vivo suggested by FIG. 4 is of the order of 15.24% per hour:

In this figure X represents time (in hours) and Y represents the percentage (%) of active principle absorbed in vivo. (Regression chosen: $1.Y=AX+B$ with $A=15.10$ and $B=3.48$ Correlation coefficient * $r=0.9886$).

FIG. 5 presents the correlation between these kinetics of absorption in vivo (FIG. 4) and the kinetics of dissolution in vitro (FIG. 2): in fact, at each of the preceding sampling times, there is a value for absorption in vivo (Y, on the ordinate) which corresponds to a value for release by dissolution in vitro (X, along the abscissa) and a significant correlation can thus be obtained.

In this figure X represents the percentage (%) dissolved in vitro and Y represents the percentage (%) absorbed in vivo. (Regression chosen: $1.Y=AX+B$ with $A=1.14$ and $B=2.94$ Correlation coefficient * $r=0.9886$).

This significant correlation between the in vitro and the in vivo data, the initial results obtained in vivo and the kinetics of release in vitro confirm the advantageous properties concerning the release of the A.P. from the tablets according to the invention.

We claim:

1. A tablet containing a homogeneous dispersion of an active agent selected from salbutamol and derivatives thereof in a hydrophilic matrix in a concentration of 1 to 10% by weight with respect to the total weight of the tablet whereby in vitro, long-term release of the active agent is achieved, which is constant and independent of pH, over a time interval of about 12 hours and in vitro, uptake kinetics of the active agent by an organism provided with said tablet of zero order over a time interval of about 6 hours, wherein the said matrix comprises at least one swelling agent and a diluent in a weight radio of swelling agent/diluent lying between 0.2 and 0.6, and wherein said diluent contains at least one intrinsic diluent and one thickening diluent.

2. Tablet according to claim 1, characterized in that the weight ratio of thickening diluent to diluent lies between 0.1 and 0.6.

3. Tablet according to claim 1, characterized in that the active principle is present in a concentration of about 3% by weight with the respect to the total weight of the tablet.

4. Tablet according to claim 2, wherein the intrinsic diluent is selected from lactose, sorbitol, mannitol, the phosphates or sulphates of calcium, colloidal silica and microcrystalline cellulose and combinations thereof.

5. Tablet according to claim 1, wherein the thickening diluent is selected from starches, microfine cellulose and dextrins.

6. Tablet according to claim 1 wherein the swelling agent is chosen from among one or more water-soluble polymeric substances of apparent viscosity lying between 0.1 and 30 Pa.s.

7. Tablet according to claim 6, characterized in that the water-soluble polymeric substance(s) are chosen from among the family of the cellulose and protein hydrocolloids.

8. Tablet according to claim 7, characterized in that the polymeric substance(s) is/are chosen from among alginate derivatives, naturally occurring gums, methylcellulose, carboxymethylcellulose, hydroxypropylcellulose and/or methylhydroxypropylcellulose.

9. Tablet according to claim 7, characterized in that the polymeric substance is methylhydroxypropylcellulose, the viscosity of which is about 15 Pa.s.

10. Tablet according to claim 1 further comprising a lubricant.

11. Tablet according to claim 9, characterized in that the lubricant is stearic acid or one of its derivatives such as magnesium stearate.

12. Tablet according to claim 1 further comprising a pharmaceutically acceptable colouring material.

13. Tablet according to claim 1, wherein said tablet is an oblong, divisible galenic form.

14. Tablet according to claims 1 & 3 and 3 to 12 possessing the following composition:

| | |
|---|---|
| salbutamol sulfate | 9.6 mg |
| methylhydroxypropylcellulose. 15 Pa.s | 86.0 mg |
| lactose | 150.0 mg |
| pregelatinized maize starch | 70.9 mg |
| colloidal silica | 2.7 mg |
| magnesium stearate | 2.7 mg |
| for a finished tablet of | 322.0 mg. |

15. Manufacturing process for a tablet containing a homogeneous dispersion of an active agent selected from salbutamol and derivatives thereof in a hydrophilic matrix whereby in vitro, long-term release of the active agent is achieved, which is constant and independent of pH, over a time interval of about 12 hours and in vivo, the uptake kinetics of the active agent by an organism provided with said tablet are of zero order over a time interval of about 6 hours, said process comprising:

1) sieving of the swelling agent, diluent and active agent;
2) mixing of the swelling agent, diluent and the active principle in a weight ratio of swelling agent, diluent lying between 0.2 and 0.6, and a weight of active agent varying between 1 and 10% by weight of the total weight of the tablet;
3) adding of a lubricant to the composition of step 2 and mixing for about 10 minutes;
4) compressing said composition of step 3 in a rotary production machine.

16. Tablet according to claim 1, wherein the weight ratio of swelling agent to diluent is equal to about 0.4.

17. Tablet according to claim 11, wherein said pharmaceutically acceptable coloring material is indigotin.

18. Method of treating an organism with salbutamol and derivatives thereof in a tablet as claimed in claim 1 in the range of 1 to 2 times per 24 hour period.

* * * * *

UNITED STATES PATENT AND TRADEMARK OFFICE
CERTIFICATE OF CORRECTION

PATENT NO. : 5,132,116
DATED : 07/21/92
INVENTOR(S) : Sournac et al.

It is certified that error appears in the above-identified patent and that said Letters Patent is hereby corrected as shown below:

On the title page:

| | | |
|---|---|---|
| Item:[22] Filed: | delete "Oct. 18, 1991" | insert --Oct. 8, 1991-- |
| col. 02, line 23 | delete "carboxymethycellulsoe" | |
| | insert --carboxymethylcellulose-- | |
| col. 02, line 26 | delete "methylhhdroxypropylcellulose" | |
| | insert --methylhydroxypropylcellulose-- | |
| col. 04, line 15 | delete "z" | insert --a-- |
| col. 04, line 49 | delete "vitro" | insert --vivo-- |
| col. 04, line 60 | delete "principle" | insert --agent-- |
| col. 05, line 17 | delete "7" | insert --8-- |
| col. 05, line 24 | delete "9" | insert --10-- |
| col. 05, line 31 | delete "claims 1 & 3 and 3 to 12" | |
| | insert --any one of claims 1 to 15-- | |
| col. 06, line 31 | delete "11" | insert --12-- |

Signed and Sealed this

Twenty-third Day of November, 1993

*Attest:*

BRUCE LEHMAN

*Attesting Officer*      *Commissioner of Patents and Trademarks*